United States Patent [19]

Siegel

[11] Patent Number: 4,828,996

[45] Date of Patent: May 9, 1989

[54] MATERIALS AND METHOD FOR IMMOBILIZING BIOLOGICALLY ACTIVE SUBSTANCES

[76] Inventor: Rolf Siegel, Waidmannsteige 1, 8700 Wurzburg, Fed. Rep. of Germany

[21] Appl. No.: 455,496

[22] Filed: Jan. 4, 1983

[51] Int. Cl.$^4$ .................... C12N 11/02; C12N 11/00; C12N 11/06

[52] U.S. Cl. .................................. 435/177; 435/174; 435/181

[58] Field of Search ............... 435/181, 174, 177, 180, 435/803; 436/531, 532, 533, 534; 422/56, 57

[56] References Cited

U.S. PATENT DOCUMENTS

| | | | |
|---|---|---|---|
| 3,909,360 | 9/1975 | Horiuchi et al. | 435/197 X |
| 3,964,973 | 6/1976 | Hradil et al. | 435/180 |
| 3,966,580 | 6/1976 | Janata et al. | 435/291 X |
| 4,066,512 | 1/1978 | Lai et al. | 435/177 X |
| 4,151,049 | 4/1979 | Janata | 435/181 X |

FOREIGN PATENT DOCUMENTS

| | | | |
|---|---|---|---|
| 0065069 | 11/1982 | European Pat. Off. | 435/177 |
| 0953414 | 3/1964 | United Kingdom | 604/5 |

OTHER PUBLICATIONS

Shaltiel, "Hydrophobic Chromatography", in *Methods In Enzymology*, vol. 34, New York, Academic Press, 1974, pp. 126–140.

The Merck Index, Windholz et al (ed.), Tend Edit., Rahway, N.J., Merck & Co., 1983, pp. 352, 353 and 760.

Folch et al, "A Simple Method for the Isolation and Purification of Total Lipides from Animal Tissues", *Journal Biological Chemistry*, vol. 226 (1957), pp. 497–509.

Streitwieser, Jr. et al, *Introduction to Organic Chemistry*, New York, MacMillan Publishing, 1976, pp. 849–850.

*Primary Examiner*—Robert J. Warden
*Assistant Examiner*—Randall E. Deck
*Attorney, Agent, or Firm*—Kane, Dalsimer, Sullivan, Kurucz, Levy, Eisele and Richard

[57] ABSTRACT

Materials and a method of their preparation are described, for use in immobilizing soluble, biologically active compounds. The material for immobilizing includes a hydrophobic, water insoluble substrate having a coating of a mixture of different amphiphilic lipoid compounds thereon. The lipoid compounds are oriented so that the hydrophilic portions are distal to the substrate and free to bond with water soluble proteins and carbohydrates.

2 Claims, No Drawings

MATERIALS AND METHOD FOR IMMOBILIZING BIOLOGICALLY ACTIVE SUBSTANCES

BACKGROUND OF THE INVENTION

1. Field of the Invention

The invention concerns materials for the immobilization of biologically active compounds such as enzymes, coenzymes, antigens, antibodies and lecithin, that is, substances with a protein and.or a carbohydrate structure. The materials of the invention may be used in procedures requiring a solid phase form of the active compound such as a matrix bound enzyme and in affinity chromatography.

2. Brief Description of the Prior Art

A protein reactive membrane is described in German DE-OS No. 25,41,308 wherein an aliphatic compound with a reactive group is partially absorbed on a hydrophobic substrate. The aliphatic compound with a reactive group is represented by n-decanol, n-hexanol, n-decanoic acid and similar compounds with labile hydrogens. It is a disadvantage that the alphatic compound must be reacted with a reactive protein compound (for example, the carcinogen epichlorohydrin) to provide a linkage with the protein. Furthermore, the reactive groups of the protein which do not take part in the linkage must be converted or neutralized in order to block further reactions. A particular disadvantage is in that the linkage of the protein onto the matrix occurs only through one functional group. This is detrimental to the biological activity of the immobilized compound. For example, the catalytically active part of an enzyme molecule can be bound to the matrix in such a way that there is steric hindrance inhibiting the enzyme. Furthermore, activity reducing conformation changes in the compound molecule occur due to the unitary length of the "spacers" and their linkage to various molecule segments.

With this invention substrates or carrier materials are provided with which the aforementioned activation and blocking steps can be eliminated and on which the biologically active substances can be bound in a physiological manner without a pronounced reduction of their biological activity.

SUMMARY OF THE INVENTION

The invention comprises materials for immobilizing biologically active compounds which comprises; a substrate having on its surface a plurality of different amphiphilic compound molecules which are oriented in such a manner that the hydrophilic portion of their molecule can establish a covalent and/or adsorptive type of bond with a protein or a carbohydrate, in an aqueous solution thereof.

DETAILED DESCRIPTION OF THE PREFERRED EMBODIMENTS OF THE INVENTION

According to the invention, and in contrast to the above-mentioned laid open patent a plurality of different amphiphilic compounds are applied on the surface of a substrate or carrier material and are oriented thereon in such a manner that the hydrophilic part of their molecule can establish a covalent and/or adsorptive type of bond with proteins or carbohydrates in aqueous solution. In view of the fact that lipoids are used (from cells or cell membranes, body fluids (like serum or secretions) it is possible to make substrate carrier material surfaces like cell membranes.

The molecule oriented application of amphiphilic compounds onto a solid surface whereby the hydrophilic part is oriented to the aqueous phase and where the hydrophobic part anchors on the solid surface due to Van der Waals forces is known. As suggested in the aforementioned laid open patent, one can suspend or dissolve the amphiphilic compounds in a substantially non-polarizing solvent, bring the solution or the suspension into intimate contact with a hydrophobic material and then remove the solvent. In this process, the hydrophilic part of the amphiphilic molecule is available for further reactions with proteins and/or carbohydrates in aqueous solution.

In the present invention, the substrate or carrier material must have a hydrophobic character. A plastic material like, for example, cross-linked polystyrene, polypropylene, polyvinyl chloride or a polycarbonate may be employed. These materials are readily available with different pore sizes, mechanical and physical characteristics and shapes.

The bond of the biologically active compound to the hydrophilic part of the amphiphilic molecule can be of a covalent or of an adsorptive type. Presumably, compounds like phosphatidylethanolamine and phosphatidylserine will establish covalent bindings with accessible amino acid groups within proteins, whereas triglyceride and cholesterin (ester) represent relatively inert compounds on the carrier surface which will bond through adsorption. For enhanced biological activity of the compounds to be bound it is particularly important that glycosphingolipoids, for example, cerebrosides and gangliosides be present on the carrier surface because they provide an immediate hydration and stabilization of the bound compound.

Due to the numerous biologically active compounds available for binding, it is understood that the percentage of the individual amphiphilic compounds which are applied onto the carrier surface must be determined by experiment so as to arrive at optimum results as far as retained biological activity is concerned. In many cases it is sufficient to apply a lipid extract from whole blood on a hydrophobic carrier surface for binding enzymes with a good retention of activity.

The following examples describe the manner and process of making and using the invention and set forth the best mode contemplated by the inventor but are not to be construed as limiting the invention.

PREPARATION

As amphiphilic compounds, a total lipid extract from whole blood was used which was obtained in accordance with the method of Folch et al (J. Folch, M. Lees and G. H. S. Stanley: J. Biol. Chem. 226, 497 (1957). Thus, 9 ml of a chloroform-methanol-mixture (2:1 v/v) were added to 1.0 ml of freshly taken EDTA blood, thoroughly shaken and finally centrifuged. The chloroform-methanol-phase was separated and washed with 0.2 volume parts of an isotonic NaCl solution. The phases were separated, the lower phase dried at room temperature under reduced pressure and stored in a refrigerator until used.

EXAMPLE 1

Application of the Amphiphilic Substances on Polystyrene

A total lipid extract obtained in accordance with the above procedure is dissolved in about 1 ml of hexane-chloroform-mixture (6:1 v/v). The bottom of cylindrical, clear polystyrene tubes (20×65) mm, Saarstedt, Nürtingen) is covered with 200 μl of the solution and allowed to stand at room temperature under a hood for a plurality of hours until the solvent has completely evaporated. The tubes were then washed with more than 100 volume parts of tap water. A thin film has formed on the bottom of the tubes which cannot be removed with water washes.

Demonstration Of The Binding Capability Of The Coated Polystyrene For:

(a) 200 μl of a 10:1 (v/v) antiserum solution of DAKO-fluorescein conjugated antiserum (against human-IgG from rabbit) (Boehringer Ingelheim Diagnistika, Garching) which is diluted with isotonic sodium chloride solution was filled into the aforementioned treated tubes closed and stored for over five days in the dark at room temperature. Subsequently, the tubes are water washed as described before. In comparison to untreated tubes, the anti-serum is firmly bound to the coated tubes.

(b) A micro spatula tip of lyophilized creatinase from rabbit muscle (Boehringer Mannheim) is dissolved in about 1 ml of an imidazol buffer mixture (0.1 mol/l imidazol buffer, pH 6.7, 20 mmol/l glucose, 10 mmol/l Mg-acetate, 2.0 mmol/l EDTA). 200 μl of this enzyme solution was filled into the aforementioned coated polystyrene tubes, closed and stored for more than eight days at room temperature and subsequently thoroughly washed.

Activity Of The Creatinase (Assay: Monotest®CK NAC Activated, Boehringer Mannheim) was as follows:

(i) immobilized in polystyrene tubes treated in accordance with the aforementioned Example 1: 100%
(ii) immobilized in polystyrene tubes treated only with 200 ul hexane-chloroform-solution (6:1 v/v) (control): 17%
(iii) immobilized in untreated polystyrene tubes (control): 0%

(c) 100 μl of lactate dehydrogenase from hog muscle (Boehringer Mannheim) suspension was dissolved in 1 ml of 0.05M phosphate buffer (pH 7.0) 200 ul aliquots were added to the aforedescribed coated polystyrene tubes which were then closed and stored for over eight days at room temperature and subsequently washed. When tested the results were as follows:

Activity Of The Lactate Dehydrogenase (Assay: Monotest®LDH Opt.: Boehringer Mannheim)

(i) immobilized in tubes prepared in accordance with Example 1: 100%
(ii) immobilized in solvent treated tubes (control): 12%
(iii) immobilized in untreated tubes (control): 0%

(d) A micro spatula tip of urease from jack beans (Boehringer Mannheim) was dissolved in about 1 ml of 0.1M phosphate buffer (pH 7.0 200 μl of the solution aliquots were added to the aforedescribed coated polystyrene tubes, processed and tested as described above. The test results were as follows:

Activity Of The Urease (Assay: Merckotest®-Urea Merck, Darmstadt):

(i) immobilized in accordance with the invention: 100%
(ii) tubes treated with the solvent (control): 4%
(iii) untreated tubes (control): 0%

EXAMPLE 2

A total lipid extract obtained from whole blood as described above was dissolved in about 1 ml of a hexane-chloroform-solution (10:1 v/v). 50 μl aliquots of the solution were placed into the cups of a microtiter plate made of polyvinyl chloride (titertek® Immunoassay-plate, Flow Laboratories, Meckenheim), and stored at room temperature for a plurality of hours until the solvent has evaporated. The plates are subsequently washed a few times with tap water. When tested as described in Example 1, supra., the binding of fluorescein conjugated antiserum can be seen.

EXAMPLE 3

0.1 volume parts of untreated Amberlite®XAD-2 (a crosslinked polystyrene; Fluka, Ulm) were added to a hexane-chloroform-methanol mixture (1:1:1 v/v/v) of dissolved total lipid extract obtained as described above. This mixture was dried for a plurality of hours in a rotating Erlenmeyer piston at room temperature, thereafter the coated beads transmitted into a chromatography column and subsequently washed with more than 100 volume parts tap water.

The immobilization of creatinase, lactate dehydrogenase and urease is obtained substantially as described in Example 1, supra. For each 1 volume part of the treated Amberlite® 2 volume parts of the aforedescribed enzyme solutions are added, the reagent container is closed and is then put into a rotating movement with the aid of a suitable apparatus for two to three days and subsequently washed. When tested for biological activity of the bound enzymes as described in Example 1, supra., a high degree of activity is observed.

What is claimed:

1. A method for preparing materials for immobilizing water soluble proteins and/or carbohydrates, which consists essentially of; providing different lipid compounds whose molecules have a hydrophobic as well as a polar portion, dissolved or suspended in a substantially non-polar solvent or solvent mixture; bringing said solvent or solvent mixture containing said lipoid compounds into contact with the surface of a hydrophobic, water-insoluble material; and subsequently removing the solvent or solvent mixture completely whereby said compounds remain bound to the water-insoluble material through the hydrophobic portion of said molecules.

2. A material for immobilizing biologically active water soluble proteins and/or carbohydrates, which comprises;
a hydrophobic, water-insoluble, substrate having coated on its surface a plurality of different amphiphilic lipid compound molecules, which are oriented so that the hydrophilic portion of the molecule is distal to the substrate and can establish a covalent and/or adsorptive bond with said protein or carbohydrate in an aqueous solution thereof and the hydrophobic portion of the molecule is attached to said substrate.

* * * * *